(12) United States Patent
Choo et al.

(10) Patent No.: US 11,975,991 B2
(45) Date of Patent: May 7, 2024

(54) NEUTRALIZATION/WATER SEPARATION DEVICE FOR ESTERIFIED PRODUCT AND NEUTRALIZATION/WATER SEPARATION METHOD FOR ESTERIFIED PRODUCT

(71) Applicant: LG CHEM, LTD., Seoul (KR)

(72) Inventors: Yeon Uk Choo, Daejeon (KR); Sung Kyu Lee, Daejeon (KR); Hyun Kyu Kim, Daejeon (KR); Chan Hyu Jin, Daejeon (KR); Hyoung Jun, Daejeon (KR); Jin Sung Park, Daejeon (KR)

(73) Assignee: LG Chem, Ltd., Seoul (KR)

( * ) Notice: Subject to any disclaimer, the term of this patent is extended or adjusted under 35 U.S.C. 154(b) by 119 days.

(21) Appl. No.: 17/604,952

(22) PCT Filed: Jul. 1, 2020

(86) PCT No.: PCT/KR2020/008577
§ 371 (c)(1),
(2) Date: Oct. 19, 2021

(87) PCT Pub. No.: WO2021/054584
PCT Pub. Date: Mar. 25, 2021

(65) Prior Publication Data
US 2022/0177407 A1   Jun. 9, 2022

(30) Foreign Application Priority Data
Sep. 19, 2019   (KR) .......... 10-2019-0115694

(51) Int. Cl.
*B01D 21/00* (2006.01)
*B01D 17/02* (2006.01)
(Continued)

(52) U.S. Cl.
CPC ............ *C02F 1/40* (2013.01); *B01D 17/0208* (2013.01); *B01D 17/0211* (2013.01);
(Continued)

(58) Field of Classification Search
CPC ............ B01D 17/0208; B01D 21/0018; B01D 21/003; B01D 21/2461; C02F 1/40
See application file for complete search history.

(56) References Cited

U.S. PATENT DOCUMENTS

| 4,283,290 A | 8/1981 | Davies |
| 5,324,853 A | 6/1994 | Jones et al. |

(Continued)

FOREIGN PATENT DOCUMENTS

| CN | 101185812 A | 5/2008 |
| CN | 101330953 A | 12/2008 |

(Continued)

OTHER PUBLICATIONS

Fukunaga K—JP-2000000405-A Fit translation—Jan. 2000 (Year: 2000).*

(Continued)

*Primary Examiner* — Bradley R Spies
(74) *Attorney, Agent, or Firm* — Bryan Cave Leighton Paisner LLP (57) ABSTRACT

A neutralization/water separation device for an esterified product including: a neutralization tank in which a crude product mixture containing alcohol and an ester compound, a neutralizing agent, and water are put to produce a neutralized mixture; a water separation tank disposed below the neutralization tank to divide the neutralization mixture into a floating layer and an aqueous layer; a partition wall extending downward from a ceiling of the water separation tank to provide a lower passage in the water separation tank; and a transfer line that transfers the neutralized mixture from the neutralization tank to the water separation tank, where the water separation tank includes: a first water separation part into which the neutralized mixture is introduced from the neutralization tank through the transfer line; and a second water separation part into which the neutralized (Continued)

mixture is introduced from the first water separation part through the lower passage, where the first water separation part and the second water separation part are partitioned by the partition wall.

11 Claims, 5 Drawing Sheets

(51) Int. Cl.
*B01D 21/02* (2006.01)
*B01D 21/24* (2006.01)
*C02F 1/40* (2023.01)
*C07C 67/56* (2006.01)

(52) U.S. Cl.
CPC ....... *B01D 21/0018* (2013.01); *B01D 21/003* (2013.01); *B01D 21/02* (2013.01); *B01D 21/10* (2013.01); *B01D 21/2461* (2013.01); *C07C 67/56* (2013.01)

(56) References Cited

U.S. PATENT DOCUMENTS

| | | | |
|---|---|---|---|
| 5,350,511 A * | 9/1994 | Sakurada | C02F 1/5245 210/205 |
| 8,802,877 B2 | 8/2014 | Cordeiro et al. | |
| 2002/0087028 A1 | 7/2002 | Hirata et al. | |
| 2002/0099165 A1 | 7/2002 | Nagar et al. | |
| 2006/0131233 A1 | 6/2006 | Gigas et al. | |
| 2009/0173232 A1 | 7/2009 | Foklvang | |
| 2010/0006488 A1 | 1/2010 | Folkvang | |
| 2010/0180768 A1 | 7/2010 | Folkvang | |
| 2012/0006201 A1 | 1/2012 | Folkvang | |
| 2013/0233807 A1 | 9/2013 | Boyle | |
| 2016/0326016 A1 | 11/2016 | Park et al. | |
| 2017/0210639 A1 | 7/2017 | Monzyk et al. | |
| 2017/0210643 A1 | 7/2017 | Sato et al. | |
| 2017/0297996 A1 | 10/2017 | Schraut et al. | |
| 2019/0263745 A1 | 8/2019 | Lee et al. | |
| 2021/0179530 A1 | 6/2021 | Kim et al. | |

FOREIGN PATENT DOCUMENTS

| | | | |
|---|---|---|---|
| CN | 101330955 A | 12/2008 | |
| CN | 204151192 U | 2/2015 | |
| CN | 205528530 U | 8/2016 | |
| CN | 205687716 U | 11/2016 | |
| CN | 205886295 U | 1/2017 | |
| CN | 108779291 A | 11/2018 | |
| EP | 0514543 A1 | 11/1992 | |
| JP | H06-45603 U | 6/1994 | |
| JP | H09-316033 A | 12/1997 | |
| JP | 2000000405 A * | 1/2000 | ............. B01D 21/01 |
| JP | 2003-144806 A | 5/2003 | |
| JP | 2003-226672 A | 8/2003 | |
| JP | 2010-95467 A | 4/2010 | |
| JP | 6180673 B1 | 8/2017 | |
| JP | 2018-118195 A | 8/2018 | |
| KR | 10-0284475 A | 4/2001 | |
| KR | 10-0563981 A | 3/2006 | |
| KR | 10-0924075 B1 | 10/2009 | |
| KR | 10-2010-0112534 A | 10/2010 | |
| WO | 95/33705 A1 | 12/1995 | |
| WO | 02/00556 A1 | 1/2002 | |
| WO | 2019/050281 A1 | 3/2019 | |

OTHER PUBLICATIONS

Kudo T—JP-2018118195-A machine translation—Aug. 2018 (Year: 2018).*

Rahman, et al. 2004. The Plasticizer Market: An Assessment of Traditional Plasticizers And Research Trends To Meet New Challenges. Prog. Polym. Sci. 29 (2004). pps. 1223-1248.

"Pump Operator" (1988), China National Petroleum Corporation Labor Bureau, Petroleum Industry Press, p. 116.

* cited by examiner

NEUTRALIZATION/WATER SEPARATION DEVICE FOR ESTERIFIED PRODUCT AND NEUTRALIZATION/WATER SEPARATION METHOD FOR ESTERIFIED PRODUCT

CROSS-REFERENCE TO RELATED APPLICATION

The present application is a National Phase entry pursuant to 35 U.S.C. § 371 of International Application No. PCT/KR2020/008577, filed on Jul. 1, 2020, and claims the benefit of and priority to Korean Patent Application No. 10-2019-0115694, filed on Sep. 19, 2019, all of which are hereby incorporated by reference in their entirety for all purposes as if fully set forth herein.

TECHNICAL FIELD

The present invention relates to a neutralization/water separation device for an esterified product and a neutralization/water separation method for an esterified product, and more particularly, to a neutralization/water separation device of an esterified product and a neutralization/water separation method for an esterified product, in which, when preparing a plasticizer, both neutralization reaction and water separation occur well to improve efficiency.

BACKGROUND ART

A phthalate-based plasticizer accounts for 92% of the global plasticizer market until the 20th century (see Mustafizur Rahman and Christopher S. Brazel "The plasticizer market: an assessment of traditional plasticizers and research trends to meet new challenges" Progress in Polymer Science 2004, 29, 1223-1248). The phthalate-based plasticizer is an additive used for imparting flexibility, durability and cold resistance mainly to polyvinyl chloride (hereinafter, referred to as PVC) and lowering the viscosity during melting to improve processability. The phthalate-based plasticizer is added in various amounts to PVC and widely used in various applications from rigid products such as rigid pipes to soft products which may be used for such as food packaging materials, blood bags, flooring materials, etc. due to its soft and good flexibility. Therefore, it is more closely related to real life than any other material, and the direct contact with the human body may not avoidable.

However, in spite of the compatibility of the phthalate-based plasticizer with PVC and its excellent capability to impart flexibility, it has been argued recently about harmfulness of the PVC product containing the phthalate-based plasticizer that the phthalate-based plasticizer may leak out of the PVC product when used in real life, and act as a presumed endocrine disrupting (environmental hormone) substance and a carcinogen of the level of heavy metals (see N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Especially, since the report about the leakage of di-(2-ethyl hexyl) phthalate (DEHP), which has been the most used phthalate-based plasticizer in the US in the 1960s, out of the PVC product, the interest in environmental hormones have been added in the 1990s and global environmental regulations as well as various studies on hazards of the phthalate-based plasticizer to human have been started.

Therefore, in order to cope with environmental hormone problems and environmental regulations due to the leakage of the phthalate-based plasticizer, many researchers have been conducting research to develop a new, alter-native, non-phthalate-based plasticizer which is free of phthalic anhydride used in the production of phthalate-based plasticizers or a leakage inhibition technology which may inhibit the leakage of the phthalate-based plasticizer to greatly reduce the hazards to human and be in accordance with environmental standards.

As a non-phthalate-based plasticizer, a terephthalate-based plasticizer has been getting the spot-light, because it is equivalent to the phthalate-based plasticizer in terms of physical properties, but is free of environmental issues. A variety of terephthalate-based plasticizers have been developed and research on the development of a terephthalate-based plasticizer having excellent physical properties, as well as researches on facilities for preparing such the terephthalate-based plasticizer have been actively conducted. In terms of process design, more efficient, economical and simple process design has been required.

DISCLOSURE OF THE INVENTION

Technical Problem

An object of the present invention is to provide a neutralization/water separation device for an esterified product and a neutralization/water separation method for an esterified product, in which, when preparing a plasticizer, both neutralization reaction and water separation occur well to improve efficiency.

The objects of the present invention are not limited to the aforementioned object, but other objects not described herein will be clearly understood by those skilled in the art from descriptions below.

Technical Solution

A neutralization/water separation device for an esterified product according to an embodiment of the present invention for achieving the above object includes: a neutralization tank in which a crude product mixture containing alcohol and an ester compound, a neutralizing agent, and water are put to produce a neutralized mixture; a water separation tank disposed below the neutralization tank to divide the neutralization mixture into a floating layer and an aqueous layer; a partition wall extending downward from a ceiling of the water separation tank to provide a lower passage in the water separation tank; and a transfer line configured to transfer the neutralized mixture from the neutralization tank to the water separation tank, wherein the water separation tank includes: a first water separation part into which the neutralized mixture is introduced from the neutralization tank through the transfer line; and a second water separation part into which the neutralized mixture is introduced from the first water separation part through the lower passage, wherein the first water separation part and the second water separation part are partitioned by the partition wall.

In addition, the neutralization/water separation device can further include a first discharge pump configured to discharge the resultant product contained in the floating layer from a sidewall of the second water separation part to the outside.

In addition, the neutralization/water separation device can further include a second discharge pump configured to discharge the precipitated salt contained in the aqueous layer from the bottom surface of the water separation tank to the outside.

In addition, the neutralization/water separation device can further include a propeller stirrer installed in the neutralization tank to stir the neutralized mixture.

In addition, the bottom surface of the water separation tank can be gradually inclined downward toward a center thereof.

In addition, the inclination can have a range of 5° to 45°.

In addition, the lower passage can have a height of 10% to 50% of a height of the partition wall.

In addition, the water separation tank can be provided in plurality.

In addition, the plurality of water separation tanks can be connected in parallel to the neutralization tank.

In addition, the neutralized mixture can be alternately introduced into the plurality of water separation tanks.

In addition, the neutralized mixture can be introduced into the plurality of water separation tanks at the same time.

A neutralization/water separation method for an esterified product according to an embodiment of the present invention for achieving the above object includes: a step of putting a crude product mixture containing alcohol and an ester compound, a neutralizing agent, and water into a neutralization tank of a neutralization/water separation device; a step of mixing the crude product mixture, the neutralizing agent, and the water to produce a neutralized mixture; a step of introducing the neutralized mixture into a first water separation part of the water separation tank, which is disposed below the neutralization tank, through a transfer line; a step of introducing the neutralized mixture into a second water separation part of the water separation tank through a lower passage; a step of dividing the neutralized mixture into a floating layer and an aqueous layer; and a step of discharging the resultant product contained in the floating layer to the outside.

In addition, in the step of producing the neutralized mixture, the neutralized mixture can be stirred using a propeller stirrer.

In addition, a bottom surface of the water separation tank can be gradually inclined downward toward a center thereof, and precipitate contained in the aqueous layer can be collected to the center of the bottom surface of the water separation tank.

Particularities of other embodiments are included in the detailed description and drawings.

Advantageous Effects

The embodiments of the present invention can have at least the following effects.

Since the neutralization tank, in which the neutralization reaction occurs, and the water separation tank, in which the water separation occurs, are provided separately, both the neutralization reaction and the water separation can occur well to improve the efficiency.

In addition, since the neutralization tank is disposed at the upper side, the water separation tank is disposed at the lower side, and the neutralized mixture naturally flows from the neutralization tank to the water separation tank by the gravity, the separate transfer pump may not be required, and thus, the total volume may not increase, the structure can be simplified, and the neutralization/water separation device can be easily installed even in the narrow space, thereby to prevent the salt from being accumulated.

The effects of the prevent invention are not limited by the aforementioned description, and thus, more varied effects are involved in this specification.

MODE FOR CARRYING OUT THE INVENTION

Advantages and features of the present invention, and implementation methods thereof will be clarified through following embodiments described with reference to the accompanying drawings. The present invention may, however be embodied in different forms and should not be construed as limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

Unless terms used in the present invention are defined differently, all terms (including technical and scientific terms) used herein have the same meaning as generally understood by those skilled in the art. Also, unless defined clearly and apparently in the description, the terms as defined in a commonly used dictionary are not ideally or excessively construed as having formal meaning.

In the following description, the technical terms are used only for explaining a specific exemplary embodiment while not limiting the present invention. In this specification, the terms of a singular form may include plural forms unless specifically mentioned. The meaning of "comprises" and/or "including" does not exclude other components besides a mentioned component.

Hereinafter, preferred embodiments will be described in detail with reference to the accompanying drawings.

Figure 1:
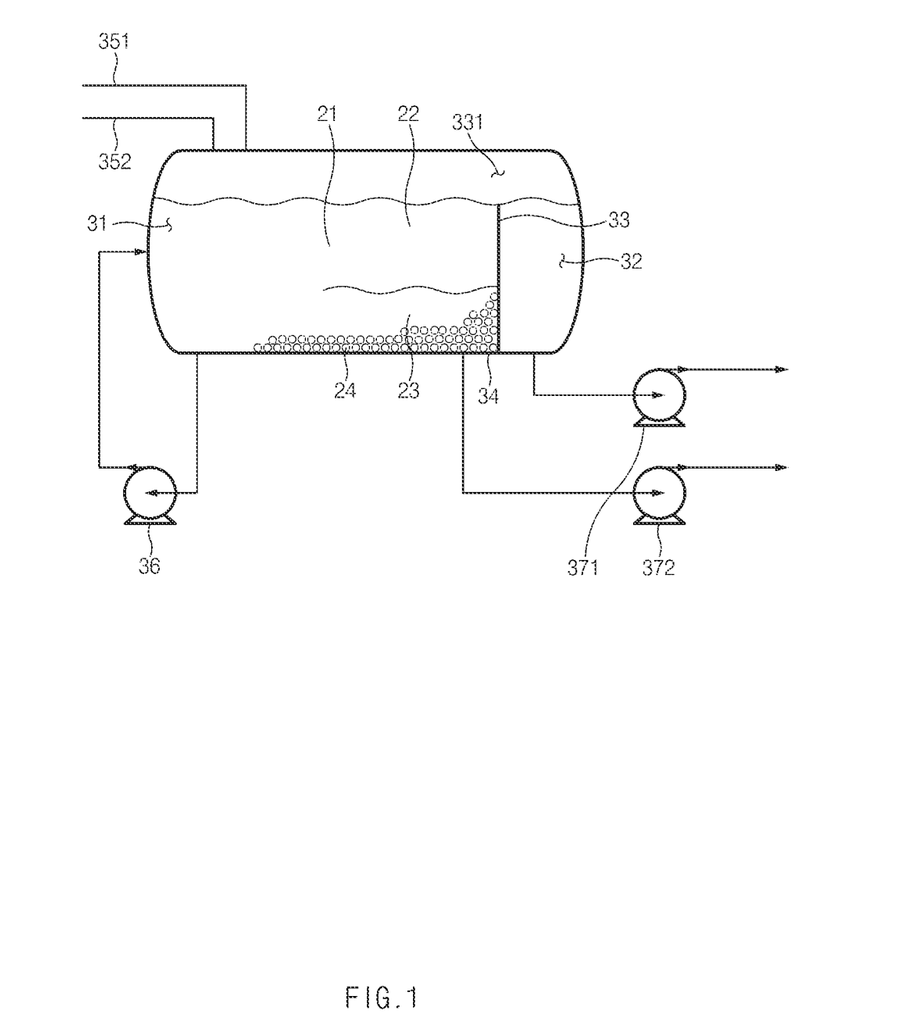
FIG. 1 is a schematic view of a neutralization/water separation tank, which is combined to allow both neutralization and water separation to occur together, according to a related art.

FIG. 1 is a schematic view of a neutralization/water separation tank 3, which is combined to allow both neutralization and water separation to occur together, according to a related art.

In order to prepare a plasticizer, a mixing step, a neutralizing step, a water-separating step, a purifying step, and a filtering step are largely performed. In the mixing step, carboxylic acid and alcohol are mixed to cause an esterification reaction, thereby producing a crude product mixture containing the alcohol and the ester compound. In the neutralizing step, a neutralizing agent that is a basic aqueous solution is mixed to the crude product mixture to neutralize the crude product mixture. In the water-separating step, the neutralized mixture is divided into a floating layer 22 containing organic matters and an aqueous layer 23 containing salt 24. In the purifying step, when the resultant product is discharged from the floating layer 22, the residual alcohol is removed. Then, in the filtering step, the resultant product is filtered using a filter to acquire a plasticizer that is a final product.

In the various steps, as illustrated in FIG. 1, the neutralization and water separation method according to the related art are performed in a neutralization/water separation tank 3 having the form of a single combined container. In addition, the inside of the neutralization/water separation tank 3 is divided into a first space 31 and a second space 32 by a partition wall 33. The partition wall 33 extends upward from a bottom surface 34 of the neutralization/water separation tank 3 to form an upper passage 331.

First, the crude product mixture is put into the first space 31 of the neutralization/water separation tank 3 through a first inlet 351, and the neutralizing agent, which is the basic aqueous solution, and water are also put into the first space 31 through a second inlet 352. Then, a circulation pump 36 connected to the first space 31 operates to mix and neutralize the crude product mixture, the neutralizing agent, and the water, thereby producing a neutralized mixture 21. Then, immediately, the mixture 21 is divided into the floating layer 22 containing the organic matters and the aqueous layer 23 containing the salt 24. When a water level of the neutralized mixture 21 is higher than that of the partition wall 33, the floating layer 22 overflows to flow into the second space 32 through the upper passage 331 disposed above the partition wall 33. Also, a first discharge pump 371 connected to the second space 32 operates to discharge the resultant product from the floating layer 22 to the outside. The salt 24 precipitated in the first space 31 does not flow into the second space 32 through the upper passage 331 and is precipitated in a lower portion of the first space 31. The precipitated salt 24 is discharged from the aqueous layer 23 to the outside by a second discharge pump 372 connected to the first space 31.

However, when external energy is applied to the neutralized mixture 21 within the first space 31 so that the neutralized mixture 21 quickly flows, the neutralization reaction may occur well. When the external energy is not applied to the neutralized mixture 21 to leave the neutralized mixture 21, the water separation may occur well. That is, since the conditions in which the neutralization reaction and the water separation occur well are contradicted, both the neutralization reaction and the water separation may not occur well, and thus, there is a problem that the efficiency is deteriorated.

Figure 2:
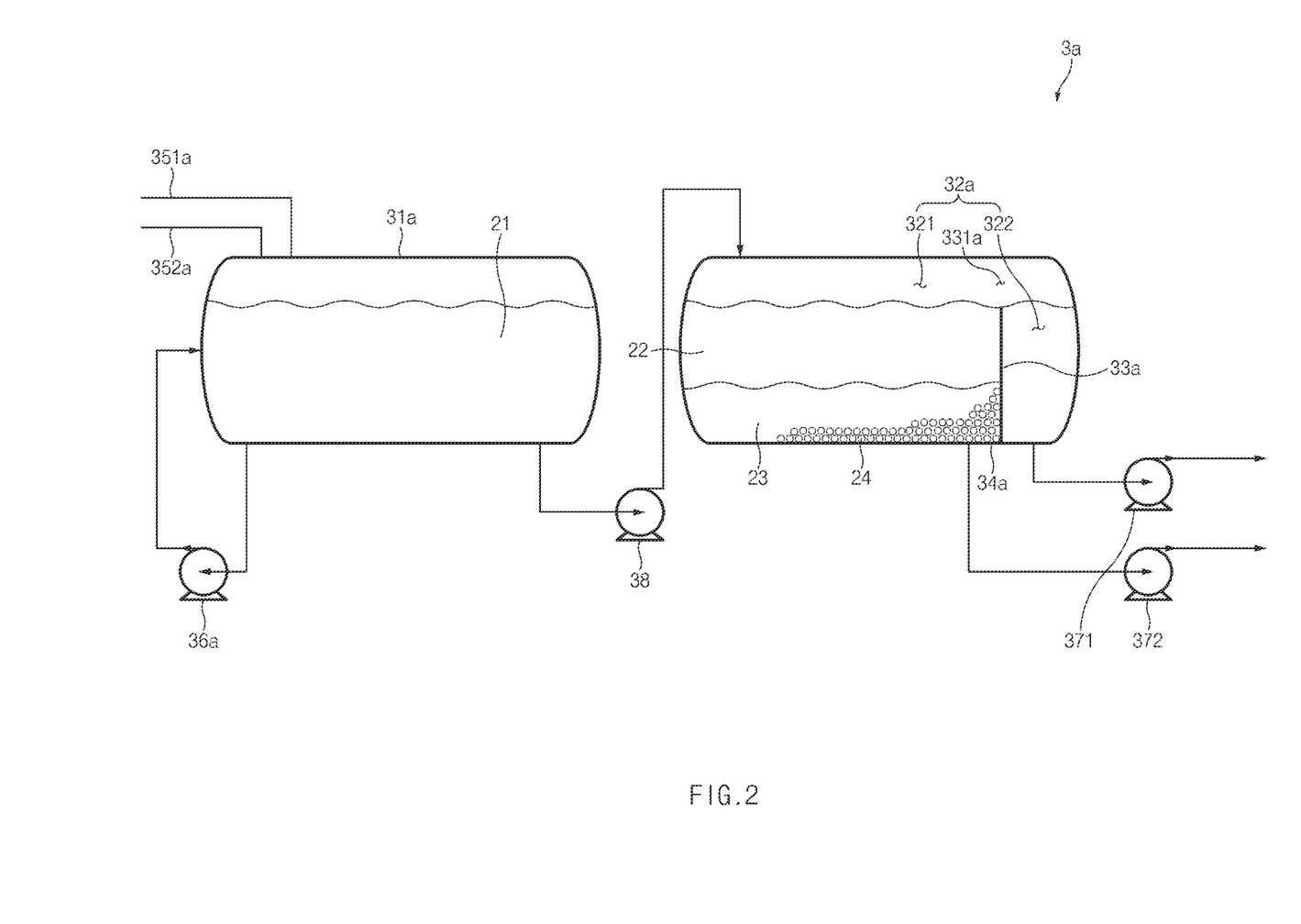
FIG. 2 is a schematic view of a neutralization/water separation device, in which a neutralization tank and a water separation tank are separated from each other, according to the related art.

FIG. 2 is a schematic view of a neutralization/water separation device 3a, in which a neutralization tank 31a and a water separation tank 32a are separated from each other, according to the related art.

In order to solve the above problem, as illustrated in FIG. 2, the neutralization tank 31a and the water separation tank 32a are separately separated from each other. That is, a crude product mixture is put into a neutralization tank 31a of the neutralization/water separation tank 3a through a first inlet 351a, and a neutralizing agent, which is a basic aqueous solution, and water are also put into the neutralization tank 31a through a second inlet 352a. Then, a circulation pump 36a connected to the neutralization tank 31a operates to mix and neutralize the crude product mixture, the neutralizing agent, and the water, thereby producing a neutralized mixture 21. Also, the neutralized mixture 21 is transferred to the water separation tank 32a by using a transfer pump 38. The inside of the water separation tank 32a is divided into a first space 321 and a second space 322 by a partition wall 33a. Also, the partition wall 33a extends upward from a bottom surface of the water separation tank 32a to form an upper passage 331a.

When the neutralized mixture 21 is put into the first space 321 through the transfer pump 38, the neutralized mixture 21 is immediately divided into a floating layer 22 containing organic matters and an aqueous layer 23 containing salt 24. When a water level of the neutralized mixture 21 is higher than that of the partition wall 33a, the floating layer 22 overflows to flow into the second space 322 through the upper passage 331a disposed above the partition wall 33a. Also, a first discharge pump 171 connected to the second space 322 operates to discharge the resultant product from the floating layer 22 to the outside. The precipitated salt 24 is discharged from the aqueous layer 23 to the outside by a second discharge pump 172 connected to the first space 321. Thus, in the neutralization tank 31a, external energy is applied to the neutralized mixture 21, and thus the neutralization reaction occurs well. In the water separation tank 32a, the external energy is not applied to the neutralized mixture 21 to leave the neutralized mixture 21, and thus the water separation occurs well to improve efficiency.

However, since the neutralization/water separation device 3a requires a separate transfer pump 38, there is a problem that a total volume increases, and the structure is complicated. In addition, when an operation of the neutralization/water separation device 3a is stopped, the neutralized mixture 21 may remain in the transfer pump 38, and the salt 24 may be precipitated. When the salt 24 is accumulated in the transfer pump, a pressure inside the transfer pump increases, and thus, the efficiency and lifespan of the pump decrease.

Figure 3:
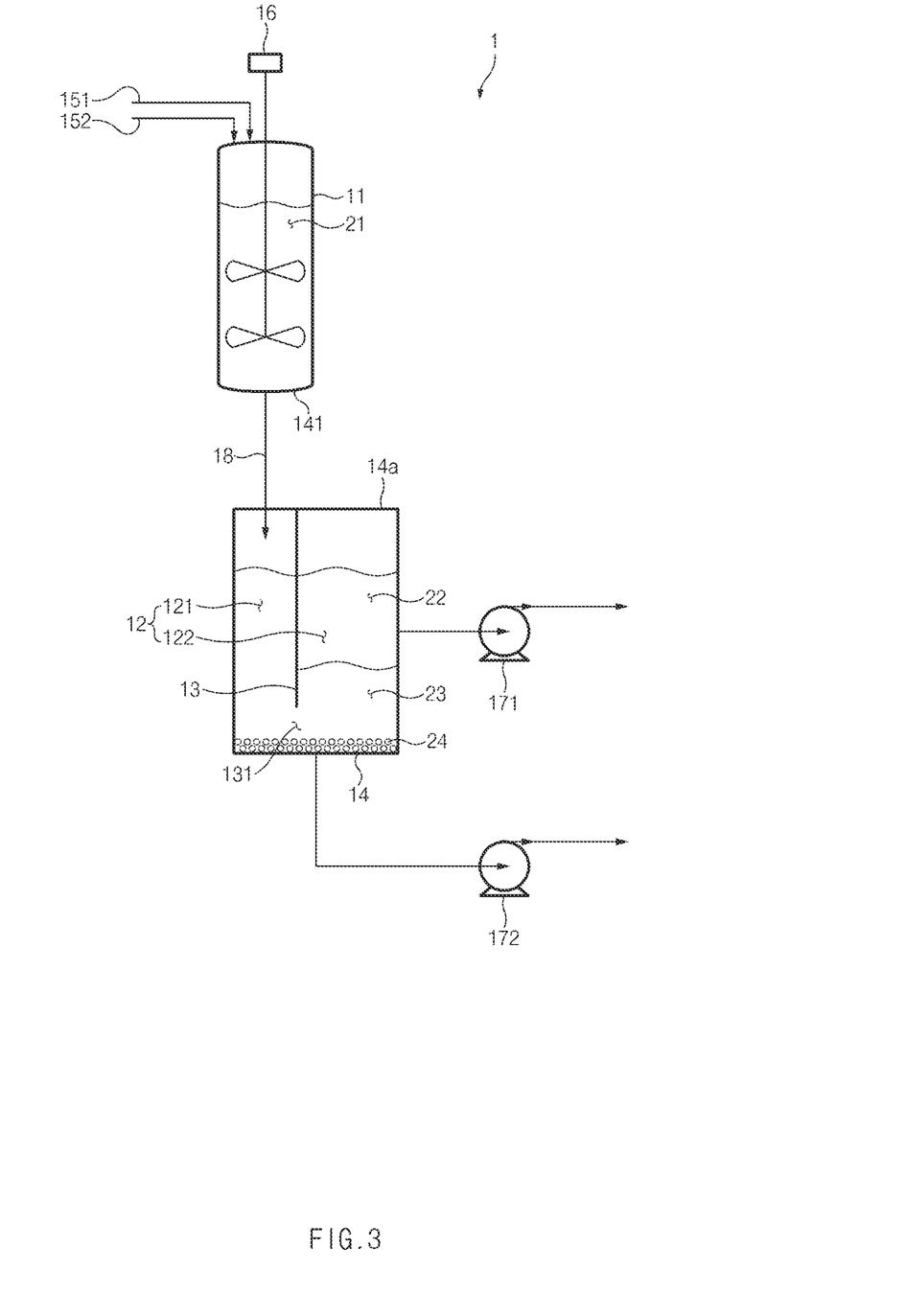
FIG. 3 is a schematic view of a neutralization/water separation device according to a first embodiment of the present invention.

FIG. 3 is a schematic view of a neutralization/water separation device 1 according to a first embodiment of the present invention.

According to a first embodiment of the present invention, since a neutralization tank 11, in which a neutralization reaction occurs, and a water separation tank in which water separation occurs, are provided to be separated from each other, both the neutralization reaction and the water separation can occur well to improve efficiency. In addition, since the neutralization tank 11 is disposed at an upper side, the water separation tank 12 is disposed at a lower side, and a neutralized mixture naturally flows from the neutralization tank 11 to the water separation tank 12 by gravity, a separate transfer pump may not be required, and thus, a total volume may not increase, a structure can be simplified, and the neutralization/water separation device 1 can be easily installed even in a narrow space, thereby to prevent salt from being accumulated.

For this, the neutralization/water separation device 1 for an esterified product according to an embodiment of the present invention includes: a neutralization tank 11 in which a crude product mixture containing alcohol and an ester compound, a neutralizing agent, and water are put to produce a neutralized mixture 21; a water separation tank 12 disposed below the neutralization tank 11 to divide the neutralization mixture 21 into a floating layer 22 and an aqueous layer 23; a partition wall 13 extending downward from a ceiling 14a of the water separation tank 12 to provide a lower passage 131 in the water separation tank 12; and a transfer line 18 configured to transfer the neutralized mixture 21 from the neutralization tank 11 to the water separation tank 12. The water separation tank 12 includes: a first water separation part 121 into which the neutralized mixture 21 is introduced from the neutralization tank 11 through the transfer line 18; and a second water separation part 122 into which the neutralized mixture 21 is introduced from the first water separation part 121 through the lower passage 131, and the first water separation part 121 and the second water separation part 122 are partitioned by the partition wall 13.

In order to prepare a plasticizer as described above, it is first subjected to a mixing step. In the mixing step, when carboxylic acid and alcohol are mixed to cause an esterification reaction, a crude product mixture containing the alcohol and the ester compound is produced.

Here, the carboxylic acid can be an alkyl carboxylic acid having 2 to 24 carbon atoms, a cycloalkyl carboxylic acid having 3 to 24 carbon atoms, an aromatic carboxylic acid having 6 to 24 carbon atoms, or a mixture thereof. For example, the carboxylic acid can be selected from caprylic acid, caproic acid, lauric acid, octanoic acid, decanoic acid, dodecanoic acid, ethanoic acid (acetic acid), propionic acid, butyric acid, pentanoic acid, hexanoic acid, ethylhexanoic acid, cyclohexane carboxylic acid, benzoic acid, cyclohexane 1,2-dicarboxylic acid, cyclohexane 1,3-dicarboxylic acid, cyclohexane 1,4-dicarboxylic acid, terephthalic acid, isophthalic acid, phthalic acid, and a combination thereof, preferably can be cyclohexane 1,2-dicarboxylic acid, cyclohexane 1,3-dicarboxylic acid, cyclohexane 1,4-dicarboxylic acid, terephthalic acid, isophthalic acid, phthalic acid, or combinations thereof, but is not limited thereto.

The alcohol can be aliphatic alcohol having a C1-C20 alkyl group, preferably aliphatic primary alcohol having a C3-C10 alkyl group. Here, the alcohols can have linear or branched alkyl and be alcohol mixed between structural isomers, and alcohols having different carbon numbers can be added as a mixture.

The esterification reaction of the alcohol component and the carboxylic acid can be performed in the presence of a catalyst. A material commonly used in the esterification reaction of alcohol can be used as the catalyst. For example, the catalyst can be one or more selected from acid catalysts such as sulfuric acid, hydrochloric acid, phosphoric acid, nitric acid, paratoluenesulfonic acid, methanesulfonic acid, ethanesulfonic acid, propanesulfonic acid, butanesulfonic acid, and alkyl sulfuric acid, metal salts such as aluminum lactate, lithium fluoride, potassium chloride, cesium chloride, calcium chloride, iron chloride, and aluminum phosphate, metal oxides such as heteropolyacids, and organic metals such as natural/synthetic zeolites, cation and anion exchange resins, tetraalkyl titanate, and polymers thereof, but is not limited thereto.

Next, a neutralizing step of neutralizing the crude product mixture with the basic neutralizing agent and a water-separating step of dividing the neutralized mixture into a floating layer 22 and an aqueous layer 23 are performed. As illustrated in FIG. 3, the neutralization/water separation method for the esterified product according to the first embodiment of the present invention is performed in the neutralization/water separation device 1 in which the neutralization tank 11 and the water separation tank 12 are separately separated from each other. Thus, external energy can be applied to only the neutralization tank 11, and thus, the neutralization reaction and the water separation can occur more efficiently.

The neutralization tank 11 provides a space in which the crude product mixture containing the alcohol and the ester compound, the neutralizing agent, and the water are put to produce the neutralized mixture 21. In the neutralization tank 11, as illustrated in FIG. 3, a propeller stirrer 16 is connected to the neutralization tank 11. The propeller stirrer 16 is a stirrer in which at least one propeller is disposed on a long rod so as to be immersed in a liquid, and the rod rotates to stir the liquid. As illustrated in FIG. 3, the propeller stirrer 16 can be provided in two, but is not limited thereto. For example, various numbers of propellers can be provided. Also, the propeller stirrer 16 can be installed substantially perpendicular to the neutralization tank 11, but is not limited thereto. For example, the propeller stirrer 16 can be installed in various manner such as being installed to be inclined or horizontally installed. The propeller stirrer 16 can be installed to quickly and uniformly stir the neutralized mixture 21.

The water separation tank 12 is disposed below the neutralization tank 11 and provides a space in which the neutralized mixture 21 is accommodated to be divided into a floating layer 22 and an aqueous layer 23. Here, the floating layer 22 is a portion that contains organic matters to serve as a plasticizer later, and the aqueous layer 23 is a portion that contains water and salt 24, which are produced by the neutralization reaction.

The transfer line 18 is connected to a bottom surface 141 of the neutralization tank 11 to transfer the neutralized mixture 21 to the water separation tank 12. Since the transfer line 18 is connected to the bottom surface 141 of the neutralization tank 11, the neutralized mixture 21 can naturally flow from the neutralization tank 11 to the water separation tank 12 by gravity without a separate transfer pump.

In the neutralization/water separation device 1 for the esterified product according to the first embodiment of the present invention, the neutralization tank 11 is disposed at an upper side, and the water separation tank 12 is disposed at a lower side. Also, the neutralized mixture 21 naturally flows from the neutralization tank 11 to the water separation tank 12 by the gravity. Thus, since the separate transfer pump for transferring the neutralized mixture 21 to the water separation tank 12 is not required, a total volume does not increase, and a structure is simplified, and salt 24 is prevented from being accumulated.

The inside of the water separation tank 12 is divided into a first water separation part 121 and a second water separation part 122 by the partition wall 13. The first water separation unit 121 provides a space by which the transfer line 18 for supplying the neutralized mixture 21 from the neutralization tank 11 and the second water separation part 122 are spaced apart from each other. In addition, the second water separation part 122 provides a space in which the neutralized mixture 21 is accommodated to be divided into the floating layer 22 and the aqueous layer 23. The neutralized mixture 21 has large kinetic energy to flow from the neutralization tank 11 into the first water separation part 121 through the transfer line 18. Also, the neutralized mixture 21 flows from the first water separation part 121 into the second water separation part 122 through the lower passage 131. Here, since the transfer line 18 and the second water separation part 122 are spaced apart from each other by the first water separation part 121, the kinetic energy of the neutralized mixture 21 is reduced in the second water separation part 122. Thus, the water separation of the neutralized mixture 21 can occur well so that the neutralized mixture 21 is more quickly and clearly divided into the floating layer 22 and the aqueous layer 23.

The partition wall 13 partitions the first water separation part 121 from the second water separation part 122. As a result, when the neutralized mixture 21 is put into the second water separation part 122, the kinetic energy can be significantly reduced, and thus the water separation can occur more efficiently. The partition wall 13 extends downward from a ceiling 14a of the water separation tank 12 to form a lower passage 131 therebelow. That is, the first water separation part 121 and the second water separation part 122 are not completely isolated by the partition wall 13 and are connected to each other through the lower passage 131. Thus, the neutralized mixture 21 put into the first water separation part 121 naturally flows into the second water separation part 122 through the lower passage 131 disposed below the partition wall 13.

It is preferable that the lower passage 131 has a height of 10% to 50% of the height of the partition wall 13. If the lower passage 131 has a height lower than 10% of the height of the partition wall 13, a flow amount of neutralized mixture 21 may be significantly reduced, and an entire process time may be excessively consumed. Also, if the lower passage 131 has a height higher than 50% of the height of the partition wall 13, since the transfer line 18 and the second water separation part 122 are not sufficiently spaced apart from each other by the first water separation part 121, the kinetic energy of the neutralized mixture 21 flowing into the second water separation part 122 may not be significantly reduced, and thus the efficiency of the water separation may be deteriorated.

A first discharge pump 171 for discharging the resultant product contained in the floating layer 22 to the outside can be connected to a sidewall of the second water separation part 122. The first discharge pump 171 is connected to the sidewall of the second water separation part 122 at a height corresponding to the position at which the floating layer 22 is floated. Since the amount of crude product mixture, neutralizing agent, and water to be put and the amount of resultant product to be discharged by the first discharge pump 171 can be adjusted through a first inlet 151 and a second inlet 152, the position at which the floating layer 22 is floated can be easily adjusted. That is, when the amount to be put increases, or the amount to be discharged decreases, the position at which the floating layer 22 is floated may increase in height, and when the amount to be put decreases, or the amount to be discharged increases, the position at which the floating layer 22 is floated may decrease in height. However, since it is preferable that the floating layer 22 is floated to a position higher than that of at least the lower passage 131, the first discharge pump 171 can be connected to a position higher than the lower passage 131.

A second discharge pump 172 for discharging the precipitated salt 24 contained in the aqueous layer 23 to the outside can be connected to the bottom surface 14 of the water separation tank 12. While the neutralized mixture 21 flows through the first water separation part 121 and the second water separation part 122, the neutralized mixture 21 can be divided into the floating layer 22 and the aqueous layer 23, and the salt 24 contained in the aqueous layer 23 can be precipitated in a lower portion of the water separation tank 12. The salt 24 is a compound in which an acidic anion and a basic cation are generated while the crude product mixture is neutralized by the neutralizing agent. Thus, the second discharge pump 172 is connected to the bottom surface 14 of the second water separation part 122 to discharge the precipitated salt 24 from the aqueous layer 23 to the outside.

A neutralization/water separation method for an esterified product according to an embodiment of the present invention includes: a step of putting a crude product mixture containing alcohol and an ester compound, a neutralizing agent, and water into a neutralization tank 11 of a neutralization/water separation device 1; a step of mixing the crude product mixture, the neutralizing agent, and the water to produce a neutralized mixture 21; a step of introducing the neutralized mixture 21 into a first water separation part 121 of the water separation tank 12, which is disposed below the neutralization tank 11, through a transfer line 18; a step of introducing the neutralized mixture 21 into a second water separation part 122 of the water separation tank 12 through a lower passage 131; a step of dividing the neutralized mixture 21 into a floating layer 22 and an aqueous layer 23; and a step of discharging the resultant product contained in the floating layer 22 to the outside.

Particularly, first, the crude product mixture containing the alcohol and the ester compound is put into the neutralization tank 11 of the neutralization/water separation device 1 through a first inlet 151, and the neutralizing agent, which is the basic aqueous solution, and water are also put into the neutralization tank 11 through a second inlet 152. Also, the crude product mixture, the neutralizing agent, and the water are mixed with each other to be neutralized, thereby producing the neutralized mixture 21. An aqueous solution of a basic substance such as alkali metal hydroxide, alkaline earth metal hydroxide, or a mixture thereof can be used as the neutralizing agent. For example, an aqueous NaOH solution or an aqueous KOH solution can be used as the neutralizing agent.

Also, the propeller stirrer 16 installed in the neutralization tank 11 operates. The propeller stirrer 16 can rotate to stir the neutralized mixture 21 of the neutralization tank 11, thereby quickly and uniformly neutralizing the neutralized mixture 21.

The neutralized mixture 21 neutralized in the neutralization tank 11 has large kinetic energy to flow from the neutralization tank 11 to the first water separation part 121 through the transfer line 18. Here, since the transfer line 18 is connected to the bottom surface 141 of the neutralization tank 11, the neutralized mixture 21 can naturally flow from the neutralization tank 11 to the water separation tank 12 by the gravity without the separate transfer pump. Also, the neutralized mixture 21 put into the first water separation part 121 naturally flows into the second water separation part 122 through the lower passage 131 disposed below the partition wall 13.

As described above, the first water separation part 121 provides a space by which the transfer line 18 and the second water separation part 122 are spaced apart from each other. Thus, since kinetic energy of the neutralized mixture introduced into the second water separation part 122 decreases, the neutralized mixture 21 is more quickly and clearly divided into the floating layer 22 and the aqueous layer 23. Also, a first discharge pump 171 connected to a sidewall of the second water separation part 122 operates to discharge the resultant product from the floating layer 22 to the outside. The discharged resultant product can be subjected to a purifying step of removing alcohol, which is the following process, and a filtering step to produce a final product, and the final product can be applied as a plasticizer. Also, a second discharge pump 172 connected to a bottom surface 14 of the water separation tank 12 discharges the salt 24 contained in the aqueous layer 23 to the outside.

In the above-described method, both the neutralization reaction and the water separation occur well to improve efficiency. In addition, since the neutralization tank 11 is disposed at an upper side, the water separation tank 12 is disposed at a lower side, and a neutralized mixture naturally flows from the neutralization tank 11 to the water separation tank 12 by gravity, a separate transfer pump may not be required, and thus, a total volume may not increase, a structure can be simplified, and the neutralization/water separation device 1 can be easily installed even in a narrow space, thereby to prevent salt from being accumulated.

Figure 4:
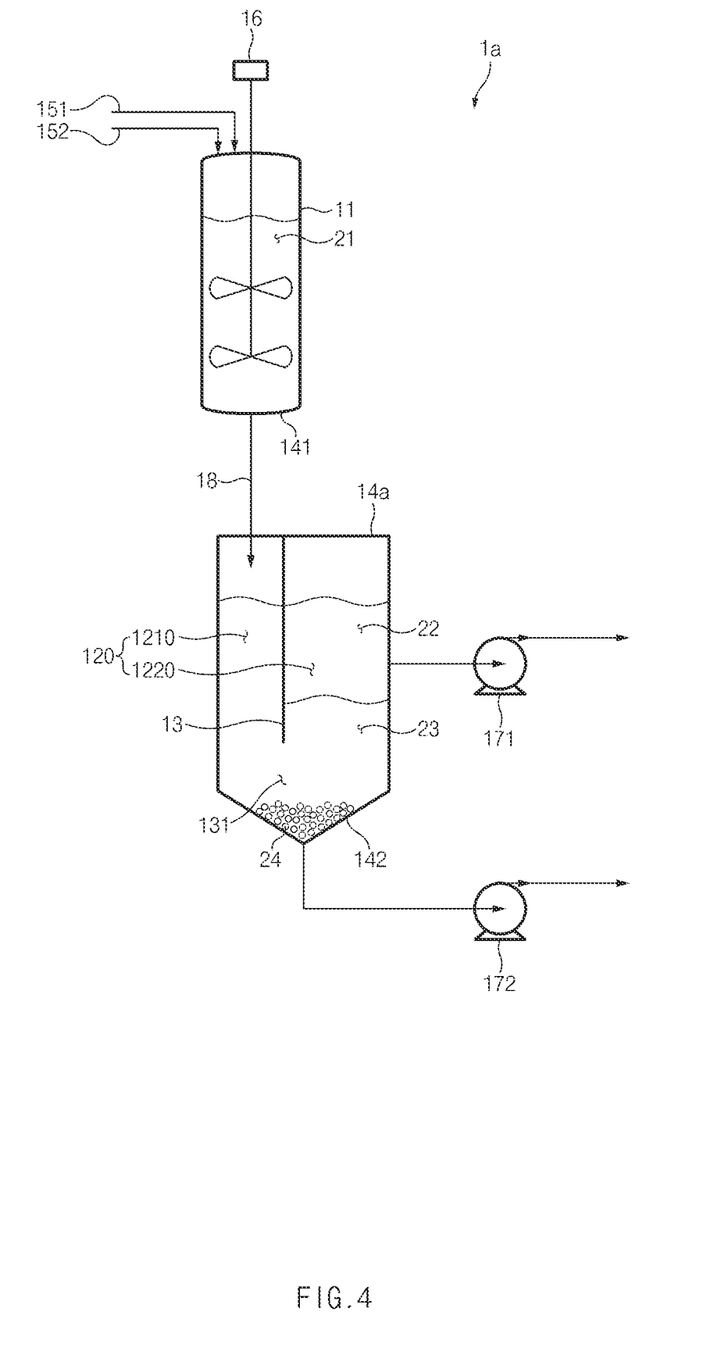
FIG. 4 is a schematic view of a neutralization/water separation tank according to a second embodiment of the present invention.

FIG. 4 is a schematic view of a neutralization/water separation tank 1a according to a second embodiment of the present invention.

According to the first embodiment of the present invention, the bottom surface 14 of each of the water separation tank 12 is flat. However, if the bottom surface 14 of the water separation tank 12 is flat, the precipitated salt 24 is dispersed on the bottom surface 14 of the water separation tank 12. Thus, it may not be easy to allow the second discharge pump 172 to discharge the salt 24 to the outside.

In the neutralization/water separation tank 1a according to the second embodiment of the present invention, a bottom surface 142 of the water separation part 120 can be gradually inclined toward a center thereof as illustrated in FIG. 4. That is, the bottom surface 142 of the water separation part 120 can have a conical shape. Also, a second discharge pump 172 can be connected to the center of the bottom surface 142 of the water separation part 120. Thus, when salt 24 is precipitated, the salt 24 is collected to the center of the bottom surface 142 of the water separation part 120, and a second discharge pump 172 can easily discharge the precipitated salt 24 to the outside.

According to the related art, when the neutralization/water separation device 3a is stopped for a long time, since the bottom surface of the neutralization tank 31a is flat, the precipitated salt 24 can be dispersed on the bottom surface of the neutralization tank 31a and then be accumulated and solidified at a corner of the bottom surface of the neutralization tank 31a. As a result, even if the neutralization/water separation device 3a operates again, the salt 24 may not be mixed with the neutralized mixture 21 to remain at the corner of the bottom surface 14 of the neutralization tank 31a.

According to embodiments of the present invention, since the neutralization tank 11 is disposed at an upper side, and the water separation tank 12 is disposed at a lower side, even if the operation of the neutralization/water separation device 1 is stopped, the neutralized mixture 21 naturally flows from the neutralization tank 11 to the water separation tank 12 by gravity. Therefore, even if the neutralization/water separation device 1 is stopped for a long time, the salt 24 may not be precipitated on the bottom surface 141 of the neutralization tank 11 to fully flow into the water separation tank 12, thereby preventing the salt 24 from being accumulated and solidified on the bottom surface 141 of the neutralization tank 11.

Figure 5:
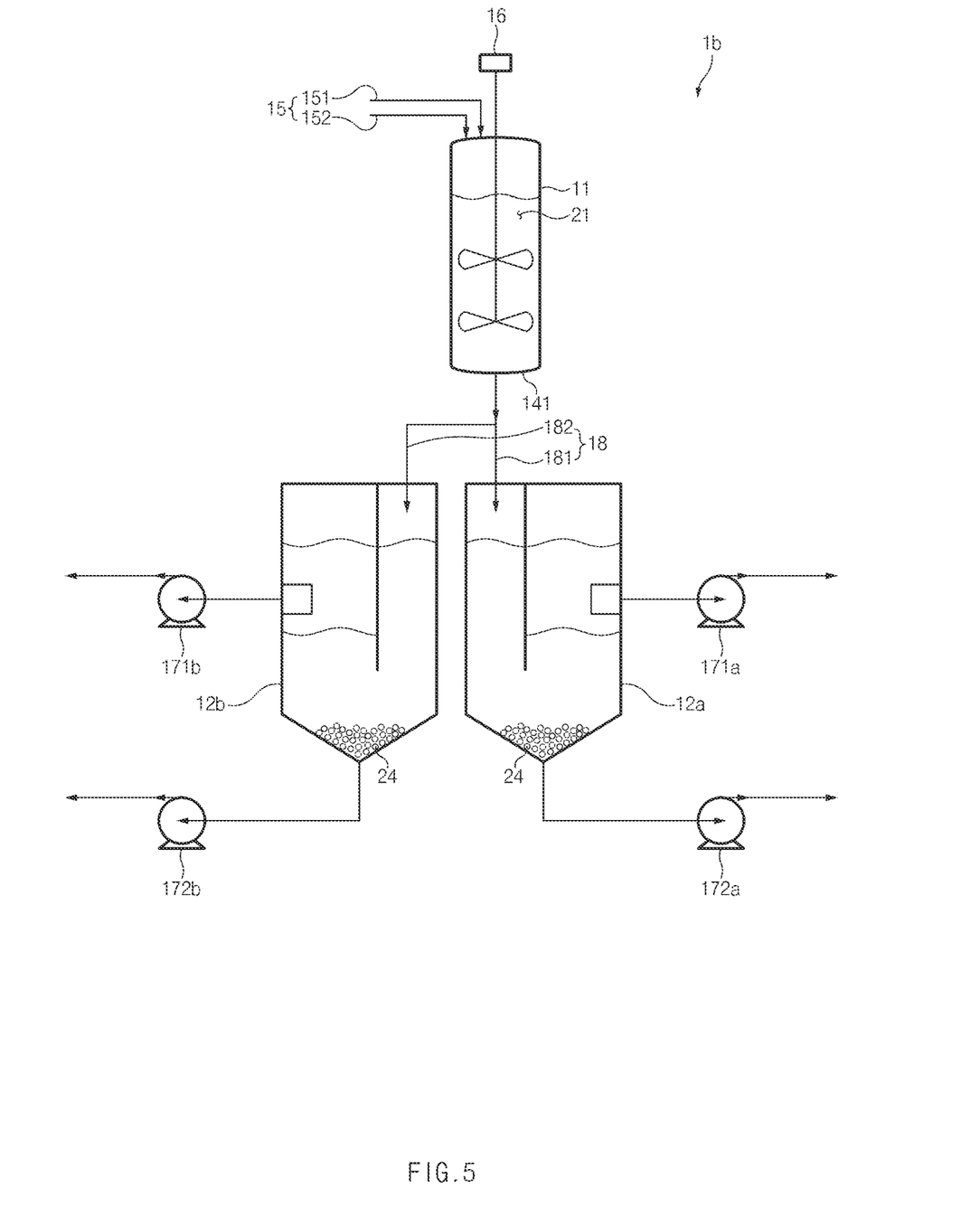
FIG. 5 is a schematic view of a neutralization/water separation tank according to a third embodiment of the present invention.

FIG. 5 is a schematic view of a neutralization/water separation tank 1b according to a third embodiment of the present invention.

As illustrated in FIG. 5, in the neutralization/water separation tank 1b according to the third embodiment of the present invention, a plurality of water separation tanks 12a and 12b are provided. Also, the plurality of water separation tanks 12a and 12b are connected in parallel to a neutralization tank 11. For this, a transfer line 18 connected from a bottom surface 141 of the neutralization tank 11 is branched into a first transfer line 181 and a second transfer line 182. Here, the first transfer line 181 is connected to a first water separation tank 12a, and the second transfer line 182 is connected to a second water separation tank 12b. Thus, when a neutralized mixture 21 is discharged from the neutralization tank 11 through the transfer line 18, the neutralized mixture 21 can be introduced into the first water separation tank 12a through the first transfer line 181 and introduced into the second water separation tank 12b through the second transfer line 182.

The neutralized mixture 21 can be alternately introduced into the plurality of water separation tanks 12a and 12b. That is, the first water separation tank 12a can serve as a main water separation tank. In general, the neutralized mixture 21 can be introduced into the first water separation tank 12a. In addition, the second water separation tank 12b can serve as a sub water separation tank. Thus, if the first water separation tank 12a is stopped due to failure, replacement, cleaning, etc., the neutralized mixture 21 can be introduced into the second water separation tank 12b. Alternatively, in order to prevent overload of the water separation tank, the neutralized mixture 21 can be alternately introduced into the first water separation tank 12a and the second water separation tank 12b at a predetermined time interval. Also, only the water separation tank 12 into which the neutralized mixture 21 is introduced and first and second discharge pumps 171 and 172, which are connected to the water separation tank 12 can operate to discharge the resultant product and the salt 24.

The neutralized mixture 21 can be introduced into the plurality of water separation tanks 12a and 12b at the same time. That is, when the neutralized mixture 21 is discharged from the neutralization tank 11 through the transfer line 18, some of the neutralized mixture 21 can be introduced into the first water separation tank 12a, and the rest of the neutralized mixture 21 can be introduced into the second water separation tank 12b. As a result, the resultant product can be more quickly discharged to significantly improve productivity.

According to the third embodiment of the present invention, as illustrated in FIG. 5, a first discharge pump 171a and a second discharge pump 172a can be connected to the first water separation tank 12a, and also, the first discharge pump 171b and the second discharge pump 172b can be separately connected to the second water separation tank 12b. Thus, even if capacity of each of the first discharge pump 171 and the second discharge pump 172 is not large, the resultant product and the salt 24 can be sufficiently discharged. However, it is not limited thereto, and if the capacity of each of the first discharge pump 171 and the second discharge pump 172 is sufficiently large, the first discharge pump 171 and the second discharge pump 172 can be respectively connected to the first water separation tank 12a and the second water separation tank 12b. That is, one first discharge pump 171 and one second discharge pump 172 can be connected to the first water separation tank 12a and the second water separation tank 12b, respectively. Therefore, the structure can be simplified, the installation can be easy, and the maintenance cost can be reduced.

Those with ordinary skill in the technical field of the present invention pertains will be understood that the present invention can be carried out in other specific forms without changing the technical idea or essential features. Therefore, the above-disclosed embodiments are to be considered illustrative and not restrictive. Accordingly, the scope of the present invention is defined by the appended claims rather than the foregoing description and the exemplary embodiments described therein. Various modifications made within the meaning of an equivalent of the claims of the invention and within the claims are to be regarded to be in the scope of the present invention.

The invention claimed is:

1. A neutralization/water separation device for an esterified product, comprising:

a neutralization tank in which a crude product mixture containing alcohol and an ester compound, a neutralizing agent, and water are put to produce a neutralized mixture;

a water separation tank disposed below a bottom surface of the neutralization tank to divide the neutralization mixture into a floating layer and an aqueous layer;

a partition wall extending downward from a ceiling of the water separation tank to provide a lower passage in the water separation tank; and a transfer line that transfers the neutralized mixture from the bottom surface of the neutralization tank to the water separation tank, wherein the water separation tank comprises:
- a first water separation part into which the neutralized mixture is introduced from the neutralization tank through the transfer line; and
- a second water separation part into which the neutralized mixture is introduced from the first water separation part through the lower passage, wherein the first water separation part and the second water separation part are partitioned by the partition wall.

2. The neutralization/water separation device of claim 1, further comprising a first discharge pump that discharges a resultant product contained in the floating layer from a sidewall of the second water separation part to the outside.

3. The neutralization/water separation device of claim 2, further comprising a second discharge pump that discharges a precipitated salt contained in the aqueous layer from a bottom surface of the water separation tank to the outside.

4. The neutralization/water separation device of claim 1, further comprising a propeller stirrer installed in the neutralization tank to stir the neutralized mixture.

5. The neutralization/water separation device of claim 1, wherein a bottom surface of the water separation tank is gradually inclined downward toward a center thereof.

6. The neutralization/water separation device of claim 5, wherein the inclination ranges from 5° to 45°.

7. The neutralization/water separation device of claim 1, wherein the lower passage has a height of 10% to 50% of a height of the partition wall.

8. The neutralization/water separation device of claim 1, wherein the water separation tank is provided in plurality.

9. The neutralization/water separation device of claim 8, wherein the plurality of water separation tanks are connected in parallel to the neutralization tank.

10. The neutralization/water separation device of claim 9, wherein the neutralized mixture is alternately introduced into the plurality of water separation tanks.

11. The neutralization/water separation device of claim 9, wherein the neutralized mixture is introduced into the plurality of water separation tanks at the same time.

* * * * *